United States Patent
Yamada (10) Patent No.: US 9,498,173 B2
(45) Date of Patent: Nov. 22, 2016

(54) MOBILE RADIATION GENERATING APPARATUS AND RADIATION IMAGING SYSTEM

(71) Applicant: CANON KABUSHIKI KAISHA, Tokyo (JP)

(72) Inventor: Naoki Yamada, Soka (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 180 days.

(21) Appl. No.: 14/258,467

(22) Filed: Apr. 22, 2014

(65) Prior Publication Data

US 2014/0321614 A1 Oct. 30, 2014

(30) Foreign Application Priority Data

Apr. 26, 2013 (JP) .................. 2013-094637

(51) Int. Cl.
*A61B 6/00* (2006.01)

(52) U.S. Cl.
CPC ............. *A61B 6/4405* (2013.01); *A61B 6/464* (2013.01); *A61B 6/465* (2013.01); *A61B 6/467* (2013.01); *A61B 6/54* (2013.01); *A61B 6/4458* (2013.01); *A61B 6/505* (2013.01)

(58) Field of Classification Search
CPC .................. A61B 6/4405; A61B 6/465; A61B 6/467; A61B 6/505; A61B 6/54; A61B 6/4283; A61B 5/415; A61B 6/56; A61B 5/0059; A61B 6/4233; A61B 5/411; A61B 5/442; A61B 5/444; A61B 5/445; A61B 6/4291; A61B 6/4423; A61B 6/548; A61B 5/418; A61B 5/443; A61B 6/00; A61B 6/037; A61B 6/44; A61B 6/4429; A61B 6/4458; A61B 6/46; A61B 6/461; A61B 6/463; A61B 6/464
USPC .................................................. 378/4, 9, 62
See application file for complete search history.

(56) References Cited

U.S. PATENT DOCUMENTS

| RE44,367 E * | 7/2013 | Aonuma ................. A61B 6/463 250/582 |
| 9,254,105 B2 * | 2/2016 | Matsumoto .............. A61B 6/00 |
| 2008/0069308 A1 * | 3/2008 | Chapman ............. A61B 6/4464 378/197 |

(Continued)

FOREIGN PATENT DOCUMENTS

JP 2003-032546 A 1/2003

*Primary Examiner* — Thomas R Artman
(74) *Attorney, Agent, or Firm* — Carter, DeLuca, Farrell & Schmidt, LLP (57) ABSTRACT

A mobile radiation generating apparatus comprising: a cart unit; a column extending from the cart unit; and an arm extending from the column; a radiation emitting unit arranged in a distal end portion of the arm, and configured to irradiate an object with radiation; a first display control unit configured to cause a first display apparatus arranged in the cart unit to display a radiation image captured by a radiation imaging apparatus which detects radiation transmitted through the object; and a second display control unit independent of the first display control unit, and configured to cause a second display apparatus arranged in the radiation emitting unit or on the arm to display a thumbnail image of the radiation image and a state of the radiation imaging apparatus.

18 Claims, 11 Drawing Sheets

(56) References Cited

U.S. PATENT DOCUMENTS

2011/0317817 A1* 12/2011 Nishino ............... A61B 6/4405
378/102
2012/0250822 A1* 10/2012 Helm ................... A61B 6/4208
378/62

* cited by examiner

મોબાઇલ રેડિએશન જનરેટિંગ એપેરેટસ એન્ડ રેડિએશન ઇમેજિંગ સિસ્ટમ
MOBILE RADIATION GENERATING APPARATUS AND RADIATION IMAGING SYSTEM

BACKGROUND OF THE INVENTION

1. Field of the Invention

The present invention relates to a mobile radiation generating apparatus and radiation imaging system for obtaining a radiation image of an object by irradiating the object with radiation.

2. Description of the Related Art

Recently, a radiation imaging system is used in various fields, and is particularly one important means for diagnoses in the medical field. The radiation imaging system in the medical field is a system in which a radiation image is obtained by irradiating an object with radiation emitted by a radiation emitting unit, and imaging radiation transmitted through the object by a radiation imaging apparatus, image processing and the like are performed on the obtained radiation image, and the processed radiation image is displayed on a monitor and used in a diagnosis.

Japanese Patent Laid-Open No. 2003-032546 has disclosed a radiation imaging system including an X-ray generating apparatus, imaging unit, and image collecting apparatus. Japanese Patent Laid-Open No. 2003-032546 has disclosed an arrangement in which the image collecting apparatus is notified of information obtained by operating an operation unit of the X-ray generating apparatus existing near an object, and processing in the image collecting apparatus is controlled based on the information.

To obtain an adequate radiation image in this radiation imaging system described in Japanese Patent Laid-Open No. 2003-032546, however, radiation must be emitted after imaging preparations of the radiation imaging apparatus have been completed. Unfortunately, the state of the radiation imaging apparatus is not displayed on the X-ray generating apparatus, so an operator cannot confirm whether the imaging preparations of the radiation imaging apparatus have been completed. To confirm the state of the radiation imaging apparatus, therefore, the operator must move to the image collecting apparatus.

The present invention has been made in consideration of the above problem, and provides a technique by which an operator can confirm an imaging result in the vicinity of an object where the operator issues an imaging instruction or the like, and can issue a next instruction on the spot.

SUMMARY OF THE INVENTION

According to one aspect of the present invention, there is provided a mobile radiation generating apparatus comprising: a cart unit; a column extending from the cart unit; and an arm extending from the column; a radiation emitting unit arranged in a distal end portion of the arm, and configured to irradiate an object with radiation; a first display control unit configured to cause a first display apparatus arranged in the cart unit to display a radiation image captured by a radiation imaging apparatus which detects radiation transmitted through the object; and a second display control unit independent of the first display control unit, and configured to cause a second display apparatus arranged in the radiation emitting unit or on the arm to display a thumbnail image of the radiation image and a state of the radiation imaging apparatus.

Further features of the present invention will be apparent from the following description of exemplary embodiments with reference to the attached drawings.

DESCRIPTION OF THE EMBODIMENTS

An exemplary embodiment(s) of the present invention will now be described in detail with reference to the drawings. It should be noted that the relative arrangement of the components, the numerical expressions and numerical values set forth in these embodiments do not limit the scope of the present invention unless it is specifically stated otherwise.

(First Embodiment)

Figure 1:
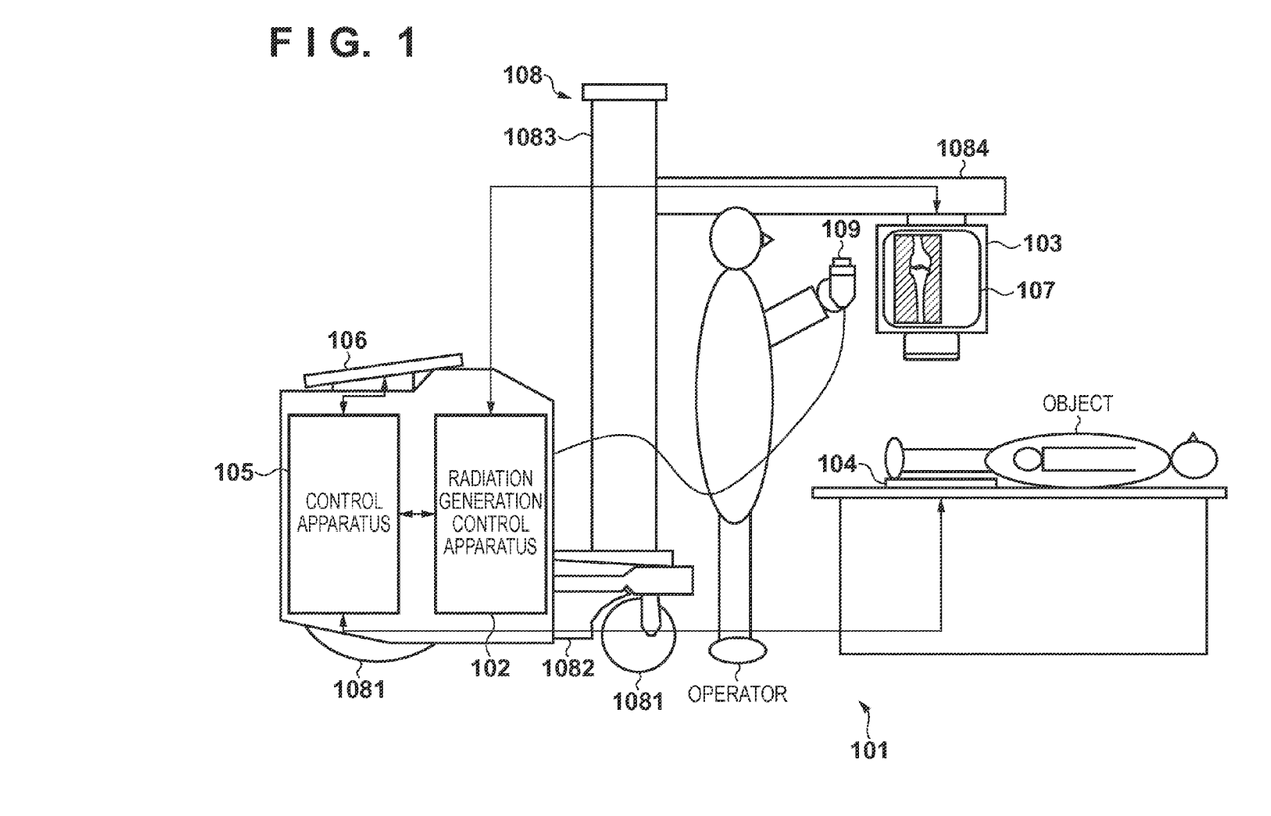
FIG. 1 is a view showing the outer appearance of a radiation imaging system according to the first embodiment.

FIG. 1 is a view showing the outer appearance of a radiation imaging system according to an embodiment of the present invention. Referring to FIG. 1, a radiation imaging system 101 is a mobile radiation imaging system, and includes a radiation generation control apparatus 102, radiation emitting unit 103, radiation imaging apparatus 104, control apparatus 105, first display apparatus 106, second display apparatus 107, car 108 for round visit, and radiation emitting switch 109. Note that an arrangement including the radiation generation control apparatus 102, radiation emitting unit 103, control apparatus 105, first display apparatus 106, second display apparatus 107, and car 108 for round visit and not including the radiation imaging apparatus 104 will be referred to as a mobile radiation generating apparatus.

The radiation generation control apparatus 102 is connected to the radiation emitting unit 103, control apparatus 105, and second display apparatus 107, and functions as a second control apparatus independent of the control apparatus 105. The radiation generation control apparatus 102 generates a high voltage. When this high voltage is applied, electrons are accelerated in the radiation emitting unit 103 and collide against a target (a rotating tube (rotating anode) or a fixed anode), thereby emitting radiation.

The radiation imaging apparatus 104 obtains a radiation image by detecting radiation emitted from the radiation emitting unit 103 and transmitted through an object. The control apparatus 105 is connected to the radiation generation control apparatus 102, radiation imaging apparatus 104, and first display apparatus 106, and controls these apparatuses.

The first display apparatus 106 displays a radiation image captured by the radiation imaging apparatus 104, and accepts operations from an operator. The second display apparatus 107 is generally made smaller than the first display apparatus 106, and displays a thumbnail image of a radiation image and some functions displayed on the first display apparatus 106.

The car 108 for round visit includes wheels 1081 for making the radiation imaging system 101 mobile, a cart unit 1082 as a main body of the car for round visit, a column 1083, and an arm 1084 that is flexible and vertically movable with respect to the column 1083. The radiation generation control apparatus 102, control apparatus 105, and first display apparatus 106 are arranged on the cart unit 1082 of the car 108 for round visit. Also, the radiation emitting unit 103 is arranged in the distal end portion of the arm 1084 of the car 108 for round visit, and the second display apparatus 107 is arranged in the radiation emitting unit 103. Note that the second display apparatus 107 may also be arranged in the radiation emitting unit 103, on the arm 1084, or on the column 1083. That is, the second display apparatus 107 can be arranged in any position where the operator can easily check the display without moving to the installation location of the first display apparatus 106.

The operator moves the car 108 for round visit near an object, and, when imaging preparations have been completed, he or she irradiates the object with radiation by using the radiation emitting switch 109 for instructing the emission of radiation.

Figure 2:
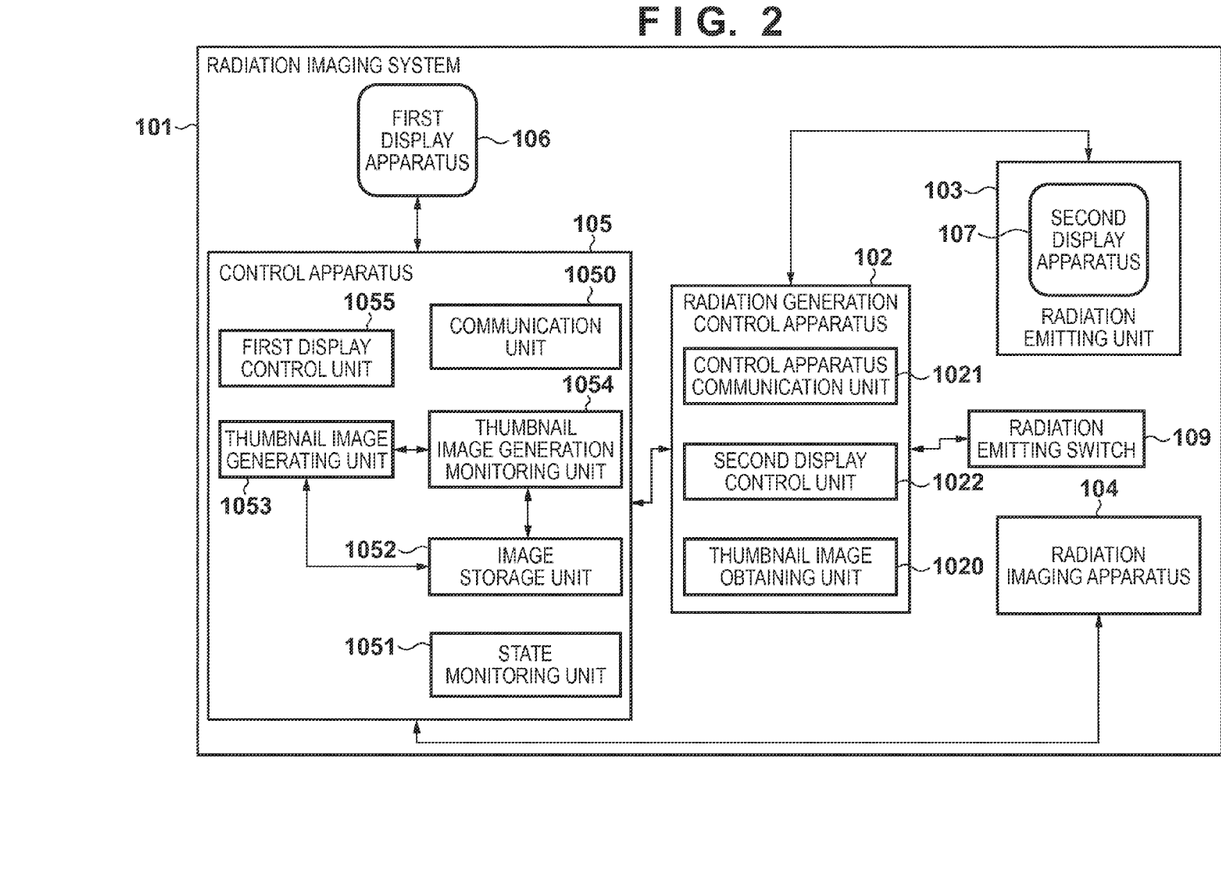
FIG. 2 is a view showing an example of the functional configuration of the radiation imaging system according to the first embodiment.

FIG. 2 is a view showing an example of the functional configuration of the radiation imaging system 101 according to the present invention. The control apparatus 105 includes a communication unit 1050, state monitoring unit 1051, image storage unit 1052, thumbnail image generating unit 1053, thumbnail image generation monitoring unit 1054, and first display control unit 1055.

The communication unit 1050 communicates with the radiation generation control apparatus 102. The state monitoring unit 1051 monitors the state of the radiation imaging apparatus 104. Examples of the state of the radiation imaging apparatus 104 are an imaging preparation completed state and imaging disabled state. The image storage unit 1052 stores a radiation image captured and transmitted by the radiation imaging apparatus 104. The image storage unit 1052 is also used to store a radiation thumbnail image (to be described later) obtained by compressing and reducing a radiation image. The thumbnail image generating unit 1053 generates a radiation thumbnail image by compressing and reducing a radiation image stored in the image storage unit 1052. The thumbnail image generation monitoring unit 1054 monitors whether the thumbnail image generating unit 1053 has generated a thumbnail image. The first display control unit 1055 controls the first display apparatus 106.

The radiation generation control apparatus 102 includes a thumbnail image obtaining unit 1020, communication unit 1021, and second display control unit 1022. The thumbnail image obtaining unit 1020 obtains a radiation thumbnail image stored in the image storage unit 1052, based on information transmitted from the control apparatus 105 and specifying a thumbnail image storage location. The communication unit 1021 communicates with the control apparatus 105. The second display control unit 1022 controls the second display apparatus 107.

Next, a radiation imaging process performed by the radiation imaging system 101 shown in FIGS. 1 and 2 will be explained. First, an operator inputs object information of an object to be imaged and examination information such as a portion to be imaged on the first display apparatus 106, thereby starting examination.

When the examination is started, the control apparatus 105 instructs the radiation generation control apparatus 102 and radiation imaging apparatus 104 to prepare for imaging. More specifically, based on the examination information input on the first display apparatus 106, the control apparatus 105 notifies the radiation generation control apparatus 102 of information pertaining to radiation generation. In addition, based on the examination information input on the first display apparatus 106, the control apparatus 105 notifies the radiation imaging apparatus 104 of information pertaining to radiation imaging.

The information pertaining to radiation generation may be information indicating conditions such as the tube voltage and tube current for generating radiation, and may also be an identification number associated with the examination information. When notifying the identification number, the radiation generation control apparatus 102 calculates condition information such as the tube voltage and tube current for generating radiation, in accordance with the notified identification number. Also, the information pertaining to radiation imaging is information indicating conditions for driving the radiation imaging apparatus 104.

The state monitoring unit 1051 monitors the state of the radiation imaging apparatus 104. The first display apparatus 106 displays the state of the radiation imaging apparatus 104 monitored by the state monitoring unit 1051. More specifically, the first display apparatus 106 displays, for example, "Ready" (imaging preparations completed) indicating that the radiation imaging apparatus 104 has completed imaging preparations, "Waiting" (imaging preparations in progress) indicating that the radiation imaging apparatus 104 is making preparations, "Capturing" (imaging in progress) indicating that the radiation imaging apparatus 104 is performing imaging, and "Not Ready" (imaging disabled) indicating that imaging is not possible other than the reasons shown above.

When the operator presses the radiation emitting switch 109 after the radiation imaging preparations have been completed, the radiation generation control apparatus 102 controls the radiation emitting unit 103 to emit radiation, and the radiation imaging apparatus 104 images the emitted radiation. The radiation image captured by the radiation imaging apparatus 104 is transmitted to the control apparatus 105, and stored in the image storage unit 1052. The control apparatus 105 performs, for example, image processing for displaying the received radiation image, and displays the processed image on the first display apparatus 106.

Also, the thumbnail image generating unit 1053 generates a radiation thumbnail image by reducing and compressing a radiation image stored in the image storage unit 1052, and stores the generated image in the image storage unit 1052. The thumbnail image generation monitoring unit 1054 monitors the state in which the thumbnail image generating unit 1053 generates a radiation thumbnail image. If the thumbnail image generation monitoring unit 1054 determines that a radiation thumbnail image is generated and stored in the image storage unit 1052, the thumbnail image generation monitoring unit 1054 transmits the generated radiation thumbnail image to the communication unit 1021 via the communication unit 1050. When receiving the radiation thumbnail image, the radiation generation control apparatus 102 displays the radiation thumbnail image on the second display apparatus 107.

Note that it is also possible to arrange the thumbnail image obtaining unit 1020 in the radiation generation control apparatus 102, refer to a radiation thumbnail image stored in the image storage unit 1052 from the radiation generation control apparatus 102, and display the radiation thumbnail image on the second display apparatus 107. More specifically, if the thumbnail image generation monitoring unit 1054 determines that a radiation thumbnail image is generated by the thumbnail image generating unit 1053 and stored in the image storage unit 1052, the communication unit 1050 notifies the communication unit 1021 of information indicating a location where the radiation thumbnail image is stored, and the thumbnail image obtaining unit 1020 displays the radiation thumbnail image on the second display apparatus 107 by referring to the location. Note that the information for specifying the storage location of a radiation thumbnail image is, for example, a file path corresponding to the radiation thumbnail image.

As described above, a radiation thumbnail image can be displayed on the second display apparatus 107 by one of the two methods. A series of radiation imaging operations are performed by the radiation imaging process as explained above.

Figure 3:
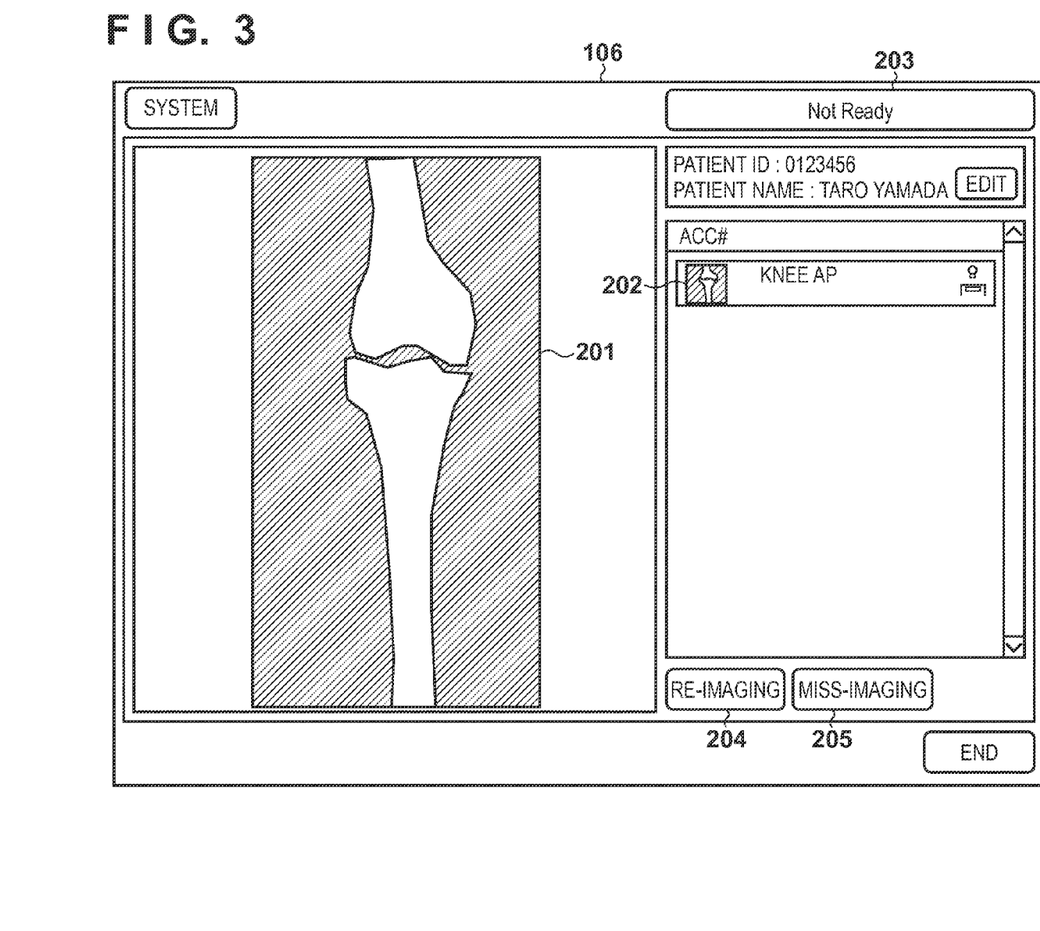
FIG. 3 is a view showing an example of a screen to be displayed on a first display apparatus according to the first embodiment.

FIG. 3 shows an example of a screen to be displayed on the first display apparatus 106. Referring to FIG. 3, reference numeral 201 denotes a radiation image displayed on the first display apparatus 106; 202, a radiation thumbnail image generated by the thumbnail image generating unit 1053; and 203, an area indicating the state of the radiation imaging apparatus 104. "Not Ready" is displayed in the area 203 in the example shown in FIG. 3. Reference numeral 204 denotes a button for instructing re-imaging for the displayed radiation image; and 205, a button for instructing miss-imaging for the displayed radiation image.

Figure 4:
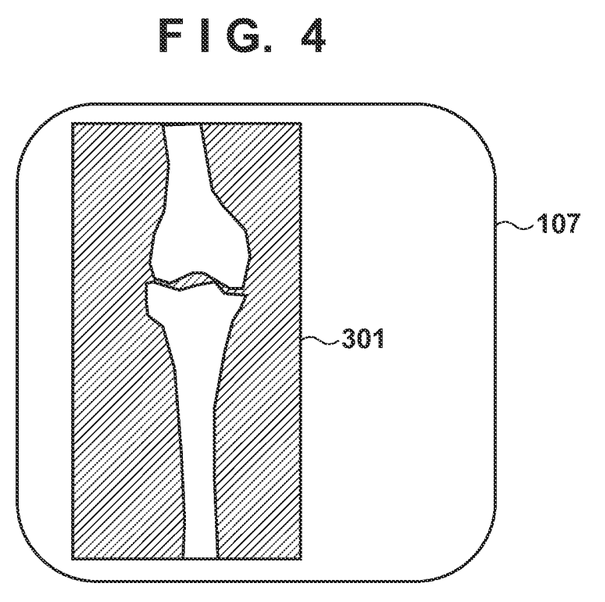
FIG. 4 is a view showing an example of a screen to be displayed on a second display apparatus according to the first embodiment.

FIG. 4 shows an example of a screen to be displayed on the second display apparatus 107. Referring to FIG. 4, reference numeral 301 denotes a radiation thumbnail image displayed on the second display apparatus 107. The radiation thumbnail image 301 is displayed on the second display apparatus 107 by one of the above-described two methods. The operator can determine whether imaging is successful by checking the radiation thumbnail image 301.

In the radiation imaging system 101, the state monitoring unit 1051 can notify, via the communication unit 1050, the communication unit 1021 of the state of the radiation imaging apparatus 104 monitored by the state monitoring unit 1051. Accordingly, the second display apparatus 107 can display the notified state of the radiation imaging apparatus 104. For example, when the radiation imaging apparatus 104 has completed imaging preparations, "Ready" can be displayed in the same manner as in the first display apparatus 106, thereby notifying the operator of the completion of the radiation imaging preparations.

Figure 5:
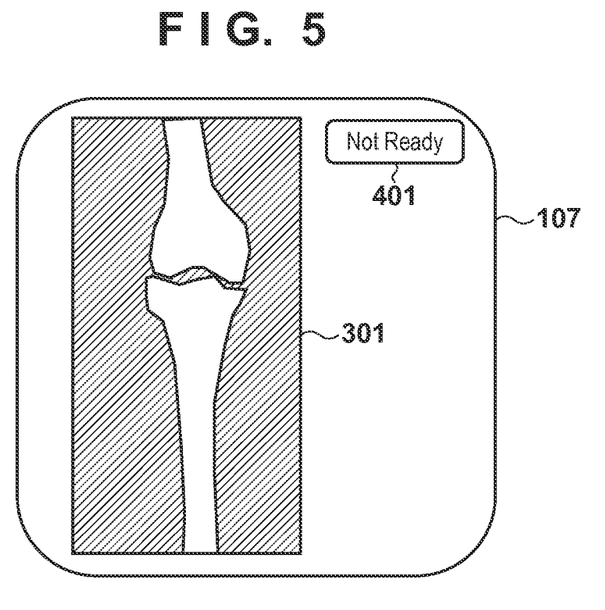
FIG. 5 is a view showing an example of the screen to be displayed on the second display apparatus according to the first embodiment.

FIG. 5 shows an example of the screen to be displayed on the second display apparatus 107 in this case. Referring to FIG. 5, reference numeral 401 denotes an area indicating the state of the radiation imaging apparatus 104 displayed on the second display apparatus 107. The area 401 displays the state of the radiation imaging apparatus 104 notified to the communication unit 1021 via the communication unit 1050 as described above. More specifically, the area 401 displays, for example, "Ready" to be displayed when the radiation imaging apparatus 104 has completed imaging preparations, "Waiting" indicating that the radiation imaging apparatus 104 is making imaging preparations, "Capturing" indicating that the radiation imaging apparatus 104 is performing imaging, and "Not Ready" indicating that an imaging disabled state.

Figure 6:
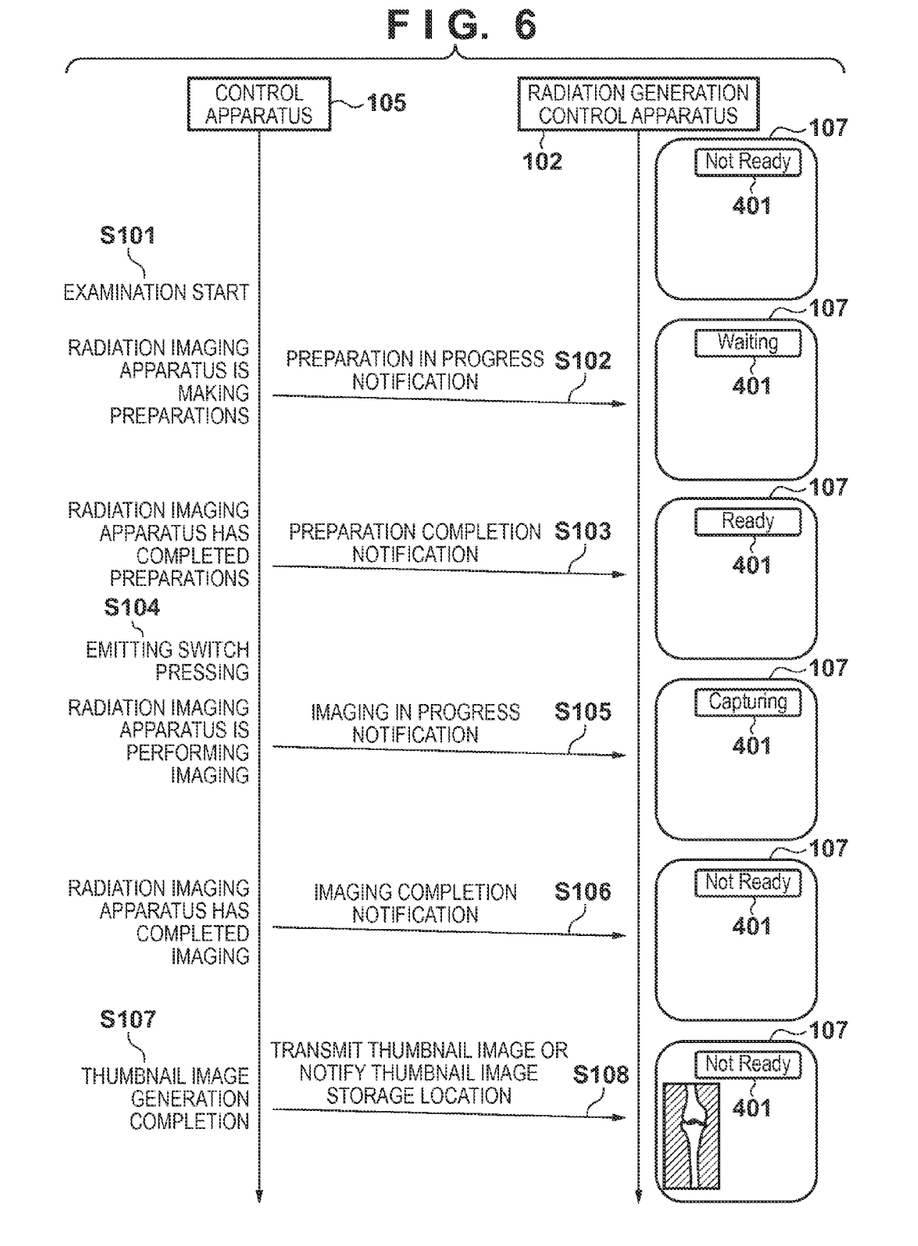
FIG. 6 is a sequence chart showing the sequence of state changes of a radiation imaging apparatus to be displayed on the second display apparatus according to the first embodiment.

FIG. 6 is a sequence chart showing the sequence of state changes of the radiation imaging apparatus 104 displayed on the second display apparatus 107. Referring to FIG. 6, the operator instructs examination start on the first display apparatus 106 (step S101). Note that in a stage before the examination is started, "Not Ready" is displayed in the area 401 under the control of the second display control unit 1022, so the operator can confirm that the radiation imaging apparatus 104 has not completed imaging preparations. When the examination is started, the control apparatus 105 instructs the radiation imaging apparatus 104 to prepare for imaging, and causes the communication unit 1050 to notify the radiation generation control apparatus 102 that the radiation imaging apparatus 104 is making imaging preparations (step S102).

By this notification, the display in the area 401 on the second display apparatus 107 changes to "Waiting", so the operator can confirm that the radiation imaging apparatus 104 is making imaging preparations. When the state monitoring unit 1051 detects that the radiation imaging apparatus 104 has completed the imaging preparations, the control apparatus 105 causes the communication unit 1050 to notify the radiation generation control apparatus 102 of the completion of the imaging preparations by the radiation imaging apparatus 104 (step S103).

By this notification, the display in the area 401 on the second display apparatus 107 changes to "Ready" under the control of the second display control unit 1022, so the operator can confirm that the radiation imaging apparatus 104 has completed the imaging preparations. After thus confirming that the radiation imaging apparatus 104 has completed the imaging preparations, the operator presses the radiation emitting switch 109, thereby emitting radiation from the radiation emitting unit 103 under the control of the radiation generation control apparatus 102 (step S104).

When the state monitoring unit 1051 detects that the radiation imaging apparatus 104 is performing imaging, the control apparatus 105 causes the communication unit 1050 to notify the radiation generation control apparatus 102 that the radiation imaging apparatus 104 is performing imaging (step S105). By this notification, the display in the area 401 on the second display apparatus 107 changes to "Capturing" under the control of the second display control unit 1022, so the operator can confirm that the radiation imaging apparatus 104 is performing imaging.

When the state monitoring unit 1051 detects that the radiation imaging apparatus 104 has completed the imaging, the control apparatus 105 notifies the radiation generation control apparatus 102 of the completion of the imaging by the radiation imaging apparatus 104 (step S106). By this notification, the display in the area 401 on the second display apparatus 107 changes to "Not Ready" under the control of the second display control unit 1022, so the operator can confirm that the radiation imaging apparatus 104 has completed the imaging.

After that, the radiation imaging apparatus 104 transmits a radiation image to the control apparatus 105 in which a radiation thumbnail image is generated by the thumbnail image generating unit 1053 and stored in the image storage unit 1052 (step S107). When the radiation thumbnail image is stored, the control apparatus 105 transmits the radiation thumbnail image to the radiation generation control apparatus 102, or notifies the radiation generation control apparatus 102 of the location where the radiation thumbnail image is stored (step S108). By this transmission or notification, the radiation thumbnail image is displayed on the second display apparatus 107.

In this embodiment, the operator can confirm the state of the radiation imaging apparatus 104 on the second display apparatus 107 by following the series of sequences as described above. This makes it possible to save the operator the trouble of moving to the first display apparatus 106 in order to confirm the state of the radiation imaging apparatus 104. Also, in this embodiment, the load can be distributed by using two controllers, that is, the control apparatus and radiation generation control apparatus. This increases the processing efficiency as well.

(Second Embodiment)

Figure 7:
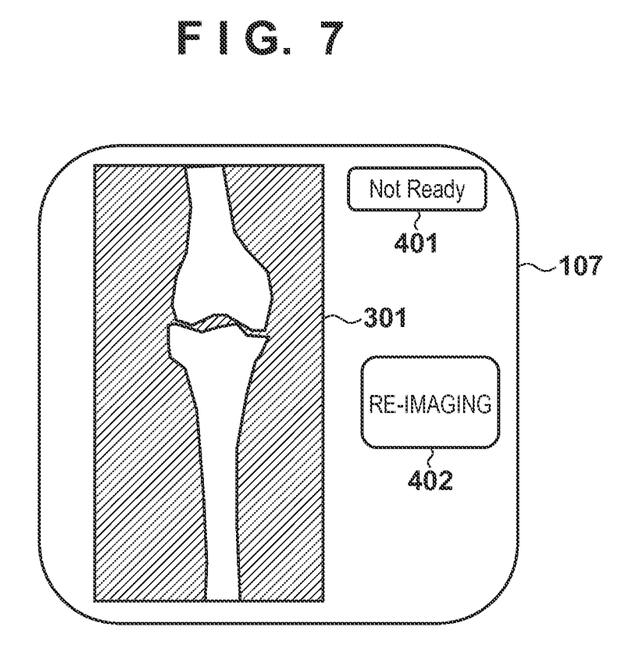
FIG. 7 is a view showing an example of a screen to be displayed on a second display apparatus according to the second embodiment.

In the second embodiment, an example in which a second display apparatus 107 instructs a re-imaging process will be explained. FIG. 7 shows an example of a screen to be displayed on the second display apparatus 107. Referring to FIG. 7, an area 402 is a GUI, and is a button by which an operator having confirmed a radiation thumbnail image displayed on the second display apparatus 107 instructs re-imaging.

Figure 8:
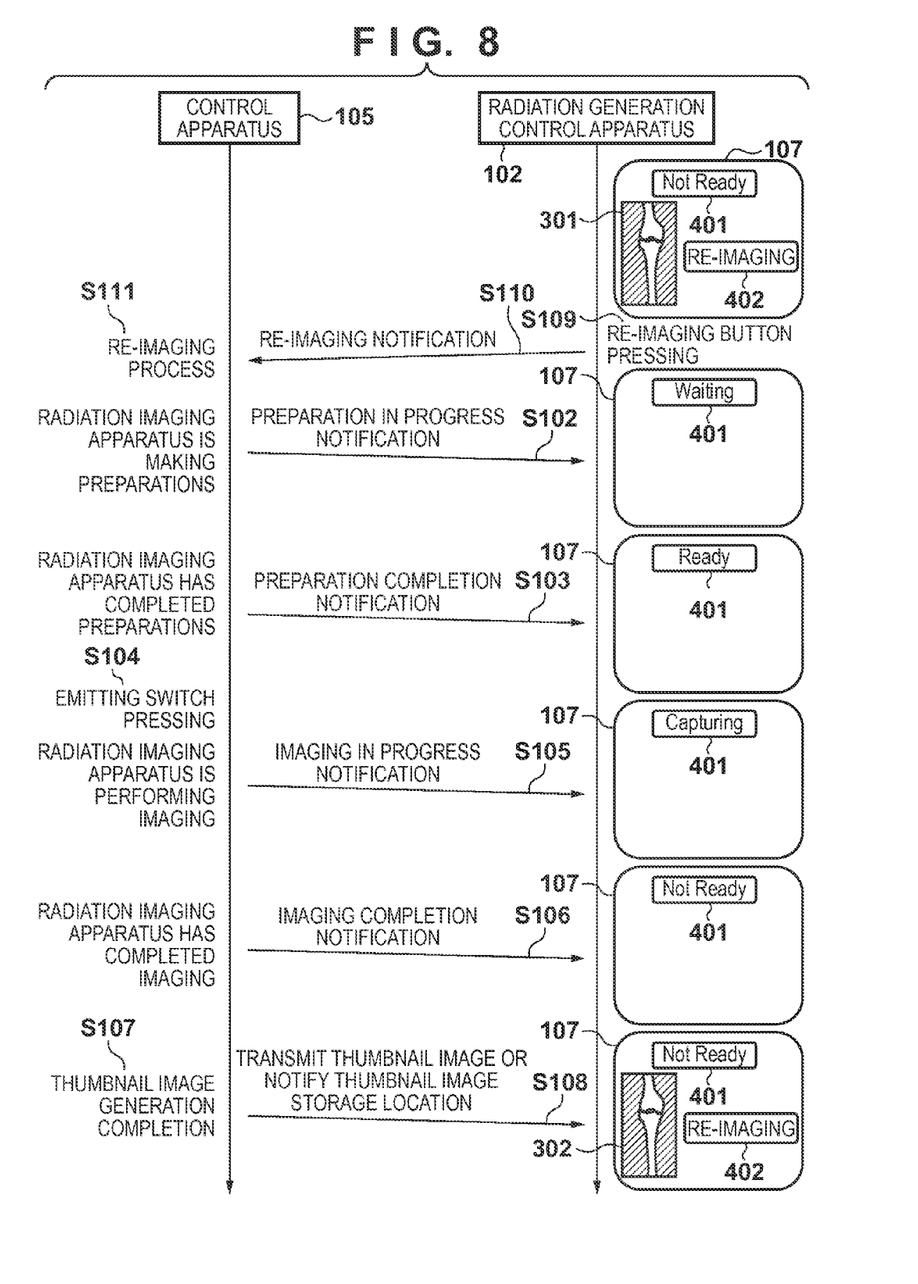
FIG. 8 is a sequence chart showing a process of instructing a re-imaging process on the second display apparatus according to the second embodiment.

If radiation imaging is unsuccessful because, for example, an object has moved, the operator instructs re-imaging, and performs imaging again. FIG. 8 is a sequence chart showing a process of instructing the re-imaging process on the second display apparatus 107. Note that the sequence shown in FIG. 8 is described as the continuation of the sequence explained with reference to FIG. 6.

Referring to FIG. 8, the operator presses the re-imaging button 402 on the second display apparatus 107, thereby instructing the re-imaging process (step S109). When the re-imaging process is instructed, a radiation generation control apparatus 102 transmits re-imaging notification to a control apparatus 105 (step S110). When receiving the re-imaging notification, the control apparatus 105 performs the re-imaging process (step S111). Processing after that is the same as in the first embodiment, so an explanation thereof will be omitted.

Figure 9:
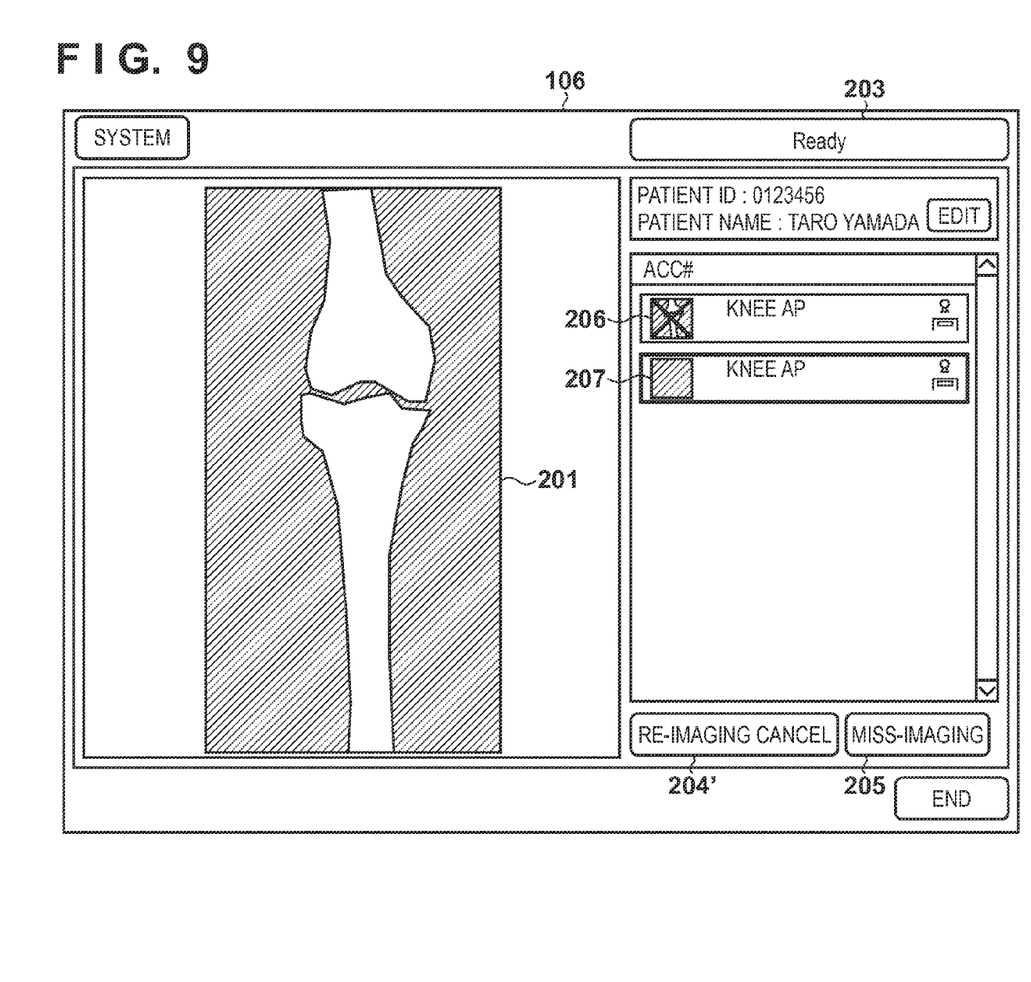
FIG. 9 is a view showing an example of a screen to be displayed on a first display apparatus when the re-imaging process according to the second embodiment is performed.

FIG. 9 shows an example of a screen to be displayed on a first display apparatus 106 by a first display control unit 1055 when the re-imaging process is performed in step S111. Based on the contents of the operation instruction (re-imaging notification) notified from the radiation generation control apparatus 102, the control apparatus 105 updates the display contents of the first display apparatus 106. Upon receiving the re-imaging notification, the control apparatus 105 displays an X mark on the radiation thumbnail image as indicated by reference numeral 206 in FIG. 9. Also, a re-imaging button 204 explained with reference to FIG. 3 changes to a button 204' for re-imaging cancellation, thereby updating the display contents. Furthermore, to perform re-imaging, the control apparatus 105 newly adds the same examination as indicated by reference numeral 207 in FIG. 9, and instructs a radiation imaging apparatus 104 to prepare for imaging. The control apparatus 105 associates a radiation image obtained by imaging regarded as a failure by the operator with information indicating failed imaging, or information indicating the prohibition of output to a specific external image management server, and stores the X-ray image in a storage unit of the control apparatus 105. After that, re-imaging is performed following the same sequence as explained with reference to FIG. 6, and a radiation thumbnail image 302 (302 in FIG. 8) obtained by the re-imaging is displayed on the second display apparatus 107 again.

By following the series of sequences as described above, the operator can instruct the re-imaging process on the second display apparatus 107. This makes it possible to save the operator the trouble of moving to the first display apparatus 106 in order to instruct the re-imaging process.

Note that the re-imaging process instructed on the second display apparatus 107 can also be canceled. For example, the re-imaging process can be canceled by pressing the re-imaging button again on the second display apparatus 107. It is also possible to cancel the re-imaging process by pressing the re-imaging canceling button 204' on the first display apparatus 106. When the re-imaging process is canceled, the first display apparatus 106 returns to the state shown in FIG. 3. Also, the second display apparatus 107 returns to the state shown in FIG. 7.

In this embodiment, a re-imaging process for a radiation image displayed on a display apparatus installed close to a radiation emitting unit can be performed on this display apparatus. Since this saves the user the trouble of returning to a display apparatus mounted on a cart unit and checking the display, the user-friendliness improves.

(Third Embodiment)

Figure 10:
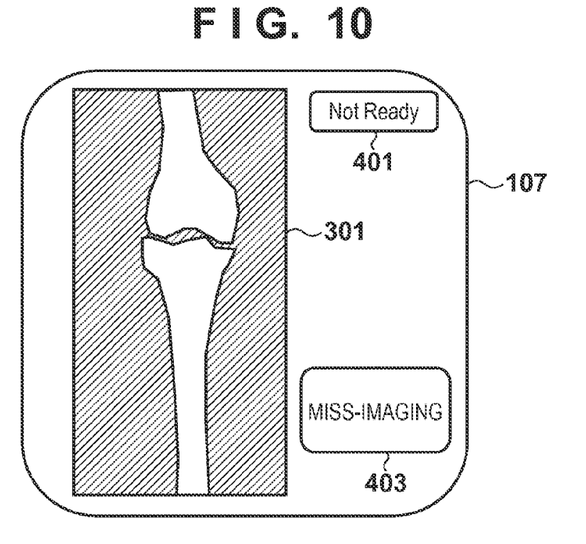
FIG. 10 is a view showing an example of a screen to be displayed on a second display apparatus according to the third embodiment.

In the third embodiment, an example in which miss-imaging processing is instructed from a second display apparatus 107 will be explained. FIG. 10 shows an example of a screen to be displayed on the second display apparatus 107 in this embodiment. Referring to FIG. 10, an area 403 is a GUI, and is a button for instructing miss-imaging for a radiation thumbnail image displayed on the second display apparatus 107.

Figure 11:
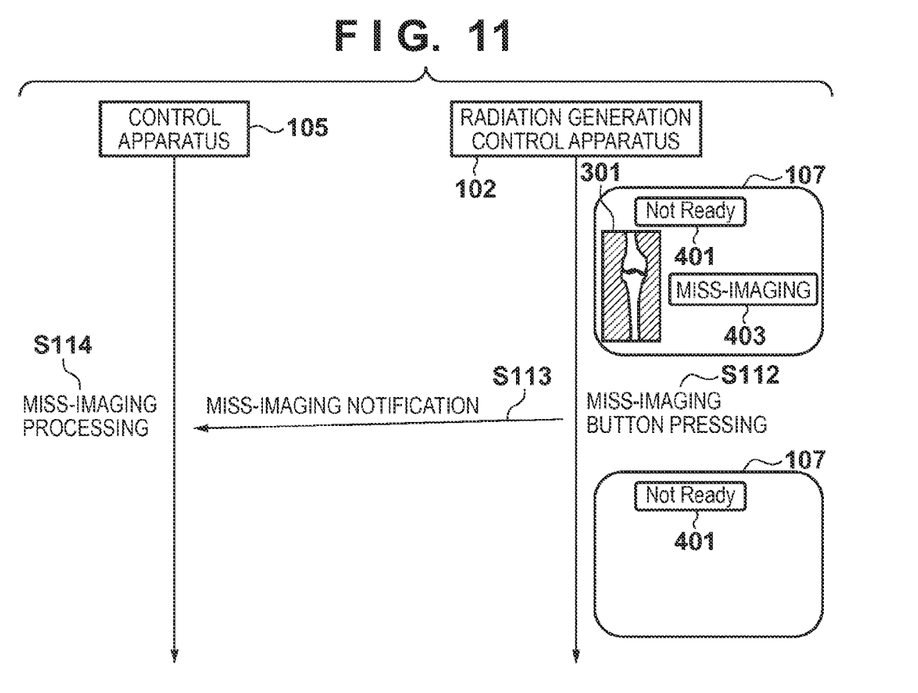
FIG. 11 is a sequence chart showing a process of instructing miss-imaging processing on the second display apparatus according to the third embodiment.

If radiation imaging is unsuccessful because, for example, an object has moved, an operator instructs miss-imaging, and invalidates the imaging itself. FIG. 11 is a sequence chart showing a process of instructing miss-imaging processing on the second display apparatus 107. Note that this sequence shown in FIG. 11 is described as the continuation of the sequence explained with reference to FIG. 6.

Referring to FIG. 11, the operator presses the miss-imaging button 403 on the second display apparatus 107, thereby instructing the miss-imaging processing (step S112). When the miss-imaging processing is instructed, a radiation generation control apparatus 102 transmits miss-imaging notification to a control apparatus 105 (step S113). Upon receiving the miss-imaging notification, the control apparatus 105 performs the miss-imaging processing (step S114).

Figure 12:
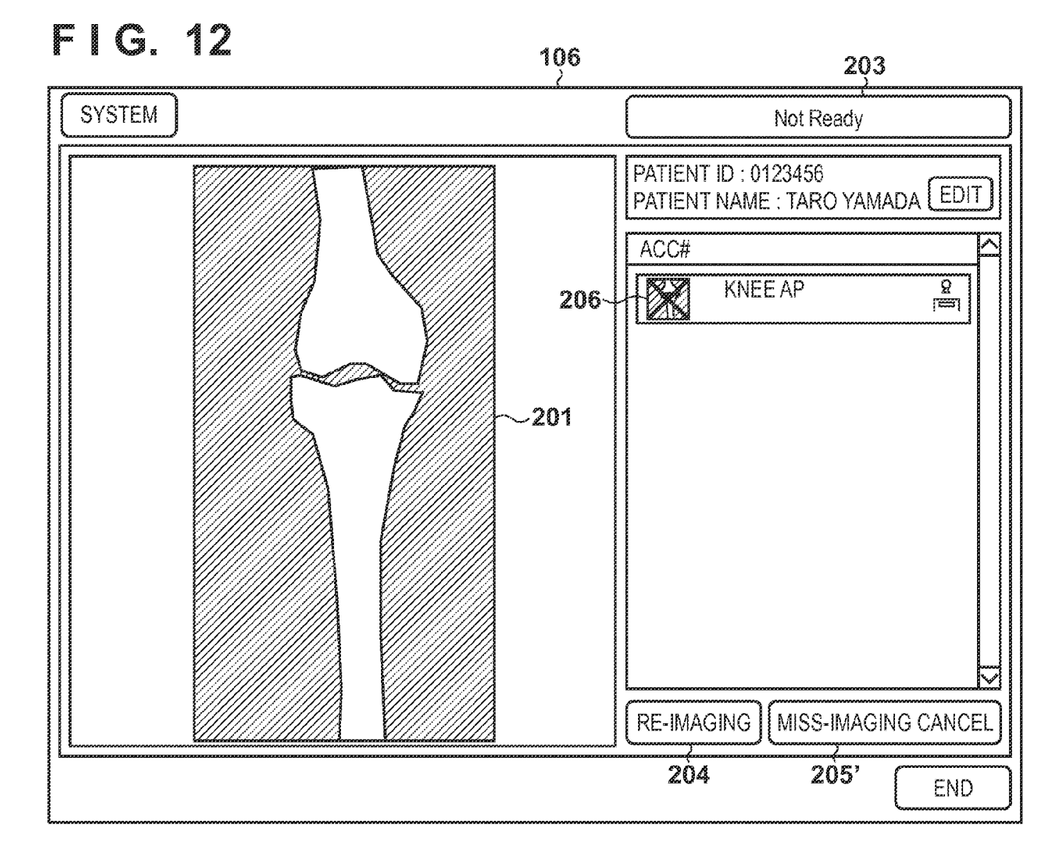
FIG. 12 is a view showing an example of a screen to be displayed on a first display apparatus when the miss-imaging processing according to the third embodiment is performed.

FIG. 12 shows an example of a screen to be displayed on a first display apparatus 106 when the miss-imaging processing is performed in step S114. Based on the contents of the operation instruction (miss-imaging notification) notified from the radiation generation control apparatus 102, the control apparatus 105 updates the display contents of the first display apparatus 106. When receiving the miss-imaging notification, the control apparatus 105 displays an X mark on a radiation thumbnail image as indicated by reference numeral 206 in FIG. 12. Also, the display contents are updated so that a miss-imaging button 205 shown in FIG. 3 changes to a button 205' for canceling miss-imaging.

By following the series of sequences as described above, the operator can instruct the miss-imaging processing on the second display apparatus 107. This makes it possible to save the operator the trouble of moving to the first display apparatus 106 in order to instruct the miss-imaging processing.

The miss-imaging processing instructed on the second display apparatus 107 can also be canceled. For example, the miss-imaging processing can be canceled by pressing the miss-imaging button again on the second display apparatus 107. It is also possible to cancel the miss-imaging processing by pressing the miss-imaging canceling button 205' on the first display apparatus 106. When the miss-imaging processing is canceled, the first display apparatus 106 returns to the state shown in FIG. 3. Also, the second display apparatus 107 returns to the state shown in FIG. 10. Note that it is also possible to display both the re-imaging button of the first embodiment and the miss-imaging button of the second embodiment on the second display apparatus 107.

(Fourth Embodiment)

In the fourth embodiment, an example in which a re-imaging process or miss-imaging processing is instructed from a first display apparatus 106 will be explained. An operator normally issues an instruction for the re-imaging process or miss-imaging processing on a second display apparatus 107 close to an object, but the number of operators using this imaging system is not always one. For example, a situation in which one operator exists near the first display apparatus 106 and another operator exists near the second display apparatus 107 is possible.

In this case, the operator near the first display apparatus 106, who is checking a larger radiation image on the first display apparatus 106, probably issues an instruction for the re-imaging process or miss-imaging processing. When the re-imaging process or miss-imaging processing is instructed from the first display apparatus 106, it is undesirable to cancel the re-imaging process or miss-imaging processing on the second display apparatus 107. Accordingly, a sequence for instructing the re-imaging process or miss-imaging processing from the first display apparatus 106 is as shown in FIG. 13.

Figure 13:
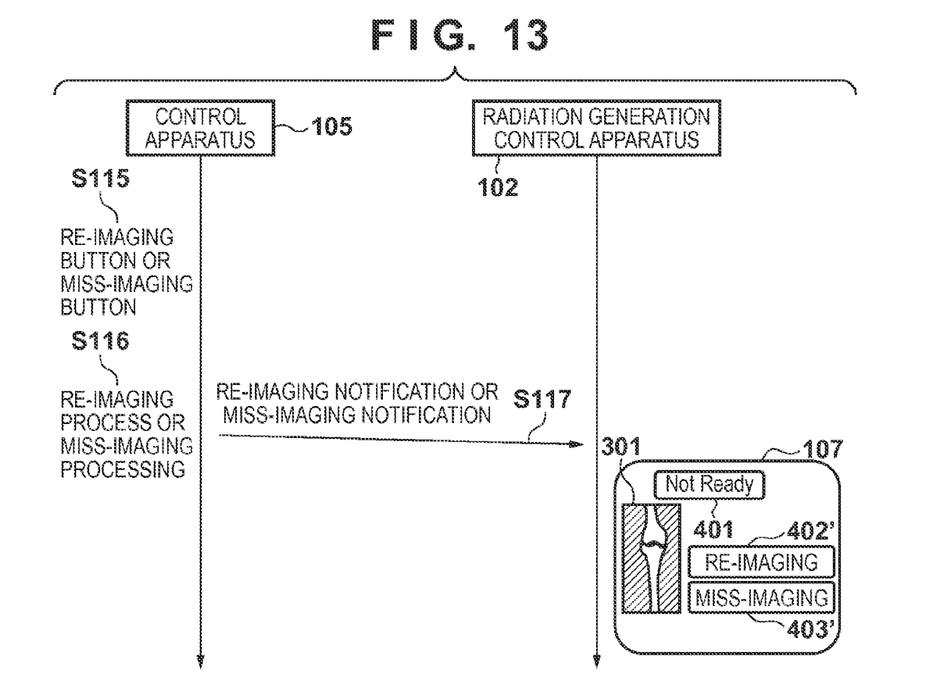
FIG. 13 is a sequence chart showing a process of instructing a re-imaging process or miss-imaging processing from a first display apparatus according to the fourth embodiment.

Referring to FIG. 13, when the operator presses a re-imaging button 204 or miss-imaging button 205 on the first display apparatus 106, a control apparatus 105 instructs the re-imaging process or miss-imaging processing (step S115). When the re-imaging process or miss-imaging processing is instructed, the control apparatus 105 performs the re-imaging process or miss-imaging processing (step S116). Furthermore, the control apparatus 105 transmits re-imaging notification or miss-imaging notification to a radiation generation control apparatus 102 (step S117). Upon receiving the re-imaging notification or miss-imaging notification, the radiation generation control apparatus 102 causes a second display control unit 1022 to perform control such that the re-imaging process or miss-imaging processing cannot be canceled on the second display apparatus 107.

Figure 14:
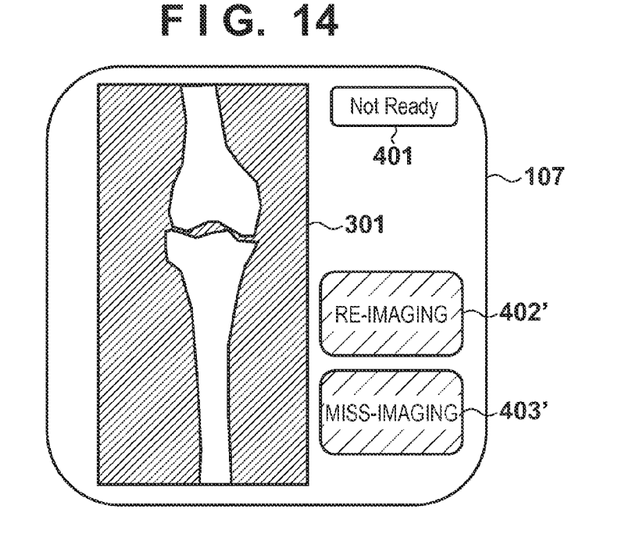
FIG. 14 is a view showing an example of a screen to be displayed on a second display apparatus when the re-imaging process or miss-imaging processing according to the fourth embodiment is made uncancelable.

FIG. 14 shows an example of a screen to be displayed on the second display apparatus 107 when the re-imaging process or miss-imaging processing is made uncancelable. For example, control is so performed as to make the re-imaging process or miss-imaging processing uncancelable on the second display apparatus 107 by invalidating a button like the re-imaging button 402' or miss-imaging button 403'.

By following the series of sequences as described above, the re-imaging process or miss-imaging processing instructed from the first display apparatus 106 can be made uncancelable on the second display apparatus 107.

In the present invention as has been explained above, a captured radiation image can be confirmed on the display apparatus connected to the radiation emitting unit by using the radiation imaging system. A re-imaging process or miss-imaging processing for the displayed radiation image can be instructed on the display apparatus.

In addition, the display apparatus connected to the radiation emitting unit can also display the state of the radiation imaging apparatus. Therefore, an operator can terminate the imaging of an object by only operating and confirming the display apparatus connected to the radiation emitting unit. Therefore, the operator need not move close to the display apparatus connected to the control apparatus. This can improve the imaging process and shorten the imaging time.

In the present invention, an operator can confirm an imaging result in the vicinity of an object where the operator issues an imaging instruction or the like, and can issue a next instruction on the spot.

(Other Embodiments)

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-094637 filed on Apr. 26, 2013, which is hereby incorporated by reference herein in its entirety.

What is claimed is:

1. A mobile radiation generating apparatus comprising:
a cart unit;
a column extending from said cart unit;

an arm extending from said column;
a radiation emitting unit arranged in a distal end portion of said arm, and configured to irradiate an object with radiation;
a first display control unit configured to cause a first display apparatus arranged in said cart unit to display a radiation image captured by a radiation imaging apparatus which detects radiation transmitted through the object;
a second display control unit independent of said first display control unit, and configured to cause a second display apparatus arranged in said radiation emitting unit or on said arm to display a thumbnail image of the radiation image and a state of said radiation imaging apparatus;
a first control apparatus including said first display control unit; and
a second control apparatus including said second display control unit,
wherein said first control apparatus further includes:
    a state monitoring unit configured to monitor the state of said radiation imaging apparatus;
    an image storage unit configured to store the radiation image captured by said radiation imaging apparatus; and
    a thumbnail image generating unit configured to generate a thumbnail image of the radiation image stored in said image storage unit, and store the thumbnail image in said image storage unit.

2. The apparatus according to claim 1, wherein said second display control unit further causes said second display apparatus to display a GUI including a re-imaging button which accepts an input for instructing re-imaging of the radiation image.

3. The apparatus according to claim 1, wherein said second display control unit further causes said second display apparatus to display a GUI including a miss-imaging button which accepts an input for instructing miss-imaging which invalidates the radiation image.

4. The apparatus according to claim 1, wherein the state of said radiation imaging apparatus is one of imaging preparations completed, imaging preparations in progress, imaging in progress, and imaging disabled.

5. The apparatus according to claim 1, wherein
said first control apparatus further includes a communication unit configured to communicate with said second control apparatus, and
said second control apparatus further includes a communication unit configured to communicate with said first control apparatus.

6. The apparatus according to claim 5, wherein said communication unit of said first control apparatus notifies said second control apparatus of the state of said radiation imaging apparatus monitored by said state monitoring unit.

7. The apparatus according to claim 5, wherein said communication unit of said first control apparatus transmits the thumbnail image generated by said thumbnail image generating unit to said second control apparatus.

8. The apparatus according to claim 5, wherein
said communication unit of said first control apparatus transmits, to said second control apparatus, information for specifying a storage location of the thumbnail image generated by said thumbnail image generating unit, and
said second control apparatus further includes a thumbnail image obtaining unit configured to obtain the thumbnail image from said image storage unit of said first control apparatus based on the information received from said first control apparatus.

9. The apparatus according to claim 5, wherein said communication unit of said second control apparatus notifies said first control apparatus of a content of an operation instruction for the thumbnail image displayed on said second display apparatus.

10. The apparatus according to claim 9, wherein said first display control unit of said first control apparatus updates a display content of said first display apparatus based on the content of the operation instruction on the second display apparatus notified from said second control apparatus.

11. A radiation imaging system comprising:
a mobile radiation generating apparatus cited in claim 1; and
said radiation imaging apparatus.

12. A mobile X-ray generating apparatus which communicates with an X-ray imaging apparatus, comprising:
a mobile cart;
an adjustable support mechanism connected to said mobile cart;
an X-ray generating unit connected to said support mechanism;
a display unit connected to said X-ray generating unit, and configured to display an X-ray image captured by an X-ray imaging apparatus and an icon;
an operation unit; and
a control unit configured to control said X-ray generating unit and said X-ray imaging apparatus by imaging conditions based on imaging conditions of the X-ray image in accordance with an operation input from said operation unit with respect to the icon,
wherein when there is an operation input with respect to the icon, said control unit associates the X-ray image with miss-imaging information, and stores the X-ray image in a storage unit.

13. The apparatus according to claim 12, further comprising another display unit connected to said mobile cart and configured to accept an operation input,
wherein if information indicating prohibition of output to a specific external image management server is associated in accordance with an operation input to the another display unit, said display unit displays a warning by accepting an operation input for canceling the association of the information.

14. The apparatus according to claim 13, wherein if information indicating prohibition of output to a specific external image management server is associated in accordance with an operation input to the another display unit, said control unit does not execute a canceling process when said display unit accepts an operation input for canceling the association of the information.

15. The apparatus according to claim 12, further comprising another display unit connected to said mobile cart and configured to accept an operation input,
wherein said control unit does not execute specific processing to be performed in accordance with an operation input to said display unit, when a specific operation input is performed for the another display unit.

16. A mobile X-ray generating apparatus which communicates with an X-ray imaging apparatus, comprising:
a mobile cart;
an adjustable support mechanism connected to said mobile cart;
an X-ray generating unit connected to said support mechanism;

a display unit connected to said X-ray generating unit, and configured to display an X-ray image captured by an X-ray imaging apparatus, imaging conditions used when capturing the X-ray image, and an icon, and accept an operation input; and a control unit configured to control said display unit to display new unused imaging conditions based on the imaging conditions in accordance with the operation input with respect to the icon, wherein when there is an operation input with respect to the icon, said control unit associates the X-ray image with miss-imaging information, and stores the X-ray image in a storage unit.

17. The apparatus according to claim 16, further comprising another display unit connected to said mobile cart and configured to accept an operation input, wherein if information indicating prohibition of output to a specific external image management server is associated in accordance with an operation input to the another display unit, said display unit displays a warning by accepting an operation input for canceling the association of the information.

18. The apparatus according to claim 17, wherein if information indicating prohibition of output to a specific external image management server is associated in accordance with an operation input to the another display unit, said control unit does not execute a canceling process when said display unit accepts an operation input for canceling the association of the information.

* * * * *